(12) United States Patent
Bor et al.

(10) Patent No.: US 8,388,609 B2
(45) Date of Patent: Mar. 5, 2013

(54) SYSTEM AND METHOD FOR MULTIBEAM SCANNING

(75) Inventors: Zsolt Bor, San Clemente, CA (US); Guy V Holland, San Clemente, CA (US)

(73) Assignee: AMO Development, LLC., Santa Ana, CA (US)

( * ) Notice: Subject to any disclaimer, the term of this patent is extended or adjusted under 35 U.S.C. 154(b) by 1078 days.

(21) Appl. No.: 12/325,923

(22) Filed: Dec. 1, 2008

(65) Prior Publication Data
US 2010/0133246 A1 Jun. 3, 2010

(51) Int. Cl.
*A61F 6/00* (2006.01)
(52) U.S. Cl. .............................. 606/5; 359/486.01; 606/4
(58) Field of Classification Search .................. 606/4–6
See application file for complete search history.

(56) References Cited

U.S. PATENT DOCUMENTS

| | | | |
|---|---|---|---|
| 4,367,009 A | 1/1983 | Suzki | |
| 4,764,930 A | 8/1988 | Bille et al. | |
| 4,884,884 A | 12/1989 | Reis | |
| 5,480,396 A | 1/1996 | Simon et al. | |
| 5,481,384 A * | 1/1996 | Kramer et al. | 359/17 |
| 5,549,632 A | 8/1996 | Lai | |
| 5,599,340 A * | 2/1997 | Simon et al. | 606/4 |
| 5,993,438 A | 11/1999 | Juhasz et al. | |
| RE37,585 E | 3/2002 | Mourou et al. | |
| 6,610,050 B2 | 8/2003 | Bille | |
| 6,635,849 B1 | 10/2003 | Okawa et al. | |
| 6,864,478 B2 * | 3/2005 | Schroder | 250/234 |
| 7,113,284 B1 * | 9/2006 | Meeks | 356/430 |
| 7,116,403 B2 * | 10/2006 | Troost et al. | 355/67 |
| 7,218,391 B2 * | 5/2007 | Meeks | 356/237.2 |
| 7,633,034 B2 | 12/2009 | Bruland et al. | |
| 2004/0008391 A1 | 1/2004 | Bowley et al. | |
| 2004/0102764 A1 * | 5/2004 | Balling | 606/5 |
| 2004/0243111 A1 | 12/2004 | Bendett et al. | |
| 2005/0282319 A1 | 12/2005 | Bruland et al. | |
| 2007/0153273 A1 | 7/2007 | Meeks | |
| 2008/0051772 A1 * | 2/2008 | Suckewer et al. | 606/5 |
| 2008/0094711 A1 | 4/2008 | Efimov | |
| 2008/0167642 A1 | 7/2008 | Palanker et al. | |
| 2008/0319427 A1 * | 12/2008 | Palanker | 606/4 |
| 2009/0109527 A1 | 4/2009 | Sasaki et al. | |

FOREIGN PATENT DOCUMENTS

EP 1271219 A1 1/2003

OTHER PUBLICATIONS

International Preliminary Report on Patentability and Written Opinion for Application No. PCT/US2009/066189, mailed on Mar. 10, 2011, 17 pages.
International Search Report for Application No. PCT/US2009/066189, mailed on Jun. 2, 2010, 8 pages.

* cited by examiner

*Primary Examiner* — Henry M Johnson, III
(74) *Attorney, Agent, or Firm* — AMO Development, LLC.

(57) ABSTRACT

System and method of photoaltering a material. The system includes a laser source operable to produce a primary pulsed beam, a holographic optical element configured to receive the primary pulsed beam and transmit a plurality of secondary beams, and a scanner operable to direct the secondary beams to the material. The secondary beams are based on the primary pulsed beam. The method includes phase shifting a pulsed laser beam to produce an input beam, holographically altering the input beam to produce a plurality of transmission beams, and scanning a portion of the material with the transmission beams.

6 Claims, 8 Drawing Sheets

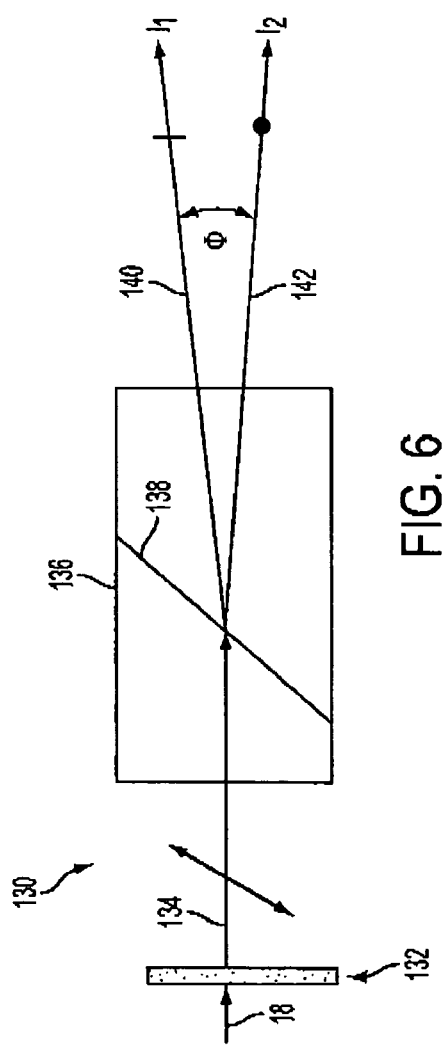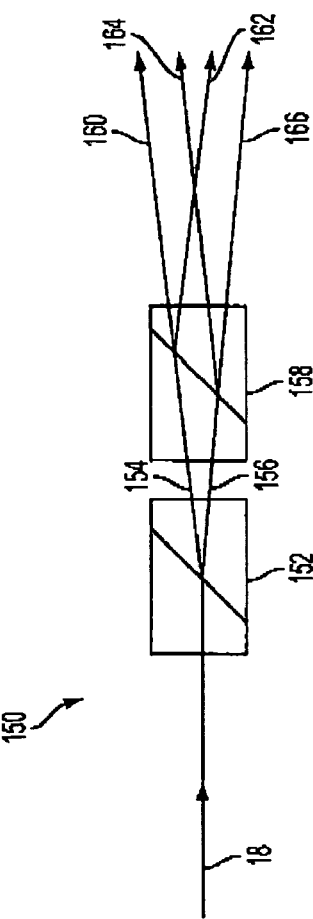

SYSTEM AND METHOD FOR MULTIBEAM SCANNING

BACKGROUND OF THE INVENTION

1. Field of the Invention

The field of the present invention is generally related to photoaltering materials and more particularly, to systems and methods for scanning pulsed laser beams.

2. Background

Pulsed laser beams include bursts or pulses of light, as implied by name, and have been used for photoalteration of materials, both inorganic and organic alike. Typically, a pulsed laser beam is focused onto a desired area of the material to photoalter the material in this area and, in some instances, the associated peripheral area. Examples of photoalteration of the material include, but are not necessarily limited to, chemical and physical alterations, chemical and physical breakdown, disintegration, ablation, vaporization, or the like.

One example of photoalteration using pulsed laser beams is the photodisruption (e.g., via laser induced optical breakdown) of a material. Localized photodisruptions can be placed at or below the surface of the material to produce high-precision material processing. For example, a micro-optics scanning system may be used to scan the pulsed laser beams to produce an incision in the material and create a flap therefrom. The term "scan" or "scanning" refers to the movement of the focal point of the pulsed laser beam along a desired path or in a desired pattern. To create a flap of the material, the pulsed laser beam is typically scanned along a region within the material at a pre-determined scan rate and with a pre-determined focal spot size.

For many applications, minimizing the scan time associated with photoalteration is generally desirable to expedite the overall procedure time. The repetition rate of the laser may be increased to generally decrease the scan time (e.g., for forming an incision in the material). In some laser systems, the repetition rate is typically limited by operating constraints of the amplifier or other components of the system. A simple increase in repetition rate may also affect other characteristics of the pulsed laser beam. For example, the pulse wavelength, the pulse duration, and the pulse intensity are inter-related. More specifically, the pulse intensity is proportional to the pulse energy and inversely proportional to the pulse duration, and the pulse energy is inversely proportional to the pulse wavelength.

Accordingly, it is desirable to provide a system and method for photoaltering a material that increases the effective repetition rate of the pulsed laser beam. It is also desirable to provide a system and method for photoaltering a material with a pulsed laser beam that improves dissection quality and while reducing scanning speed associated with the photoalteration. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is directed towards photoaltering a material using a pulsed laser beam. In one embodiment, system is provided for photoaltering a material. The system includes a laser source operable to produce a primary pulsed beam, a holographic optical element configured to receive the primary pulsed beam and transmit a plurality of secondary beams, and a scanner operable to direct the plurality of secondary beams to the material. The plurality of secondary beams is based on the primary pulsed beam.

In another embodiment, the system includes a laser source operable to produce a primary pulsed beam, a first optical element configured to receive the primary pulsed beam and transmit a first secondary beam, a first polarizing beam splitter configured to reflect a first polarized beam and transmit a second polarized beam, a subsystem configured to produce a first transmission beam and a second transmission beam based on the first and second polarized beams, and a scanner operable to direct the first and second transmission beams to the material. The first secondary beam is based on the primary pulsed beam and phase shifted from the primary pulsed beam by about a first quarter wavelength. The first and second polarized beams are together based on the first secondary beam. The first transmission beam is angularly separated from the second transmission beam.

In another embodiment, the system includes a laser source operable to produce a primary pulsed beam, an optical element having a reflectivity less than about 100%, a mirror oriented non-parallel to the optical element, and a scanner operable to direct the first and second transmission beams to the material. The optical element is configured to receive the primary pulsed beam, reflect a first transmission beam, and transmit a secondary beam. The first transmission beam and the secondary beam are together based on the primary pulsed beam. The mirror is configured to reflect the secondary beam to the optical element, and the optical element is further configured to transmit a second transmission based on the secondary beam.

In another embodiment, the system includes a laser source operable to produce a primary pulsed beam, an optical element configured to receive the primary pulsed beam and transmit a phase shifted beam, a first Wollaston prism configured to receive the phase shifted beam and transmit a first secondary beam and a second secondary beam, and a scanner operable to direct a first transmission beam and a second transmission beam to the material. The phase shifted beam is orthogonally polarized with the primary pulsed beam. The first and second secondary beams are together based on the phase shifted beam, and the first secondary beam angularly separated from the second secondary beam. The first and second transmission beams are based on the first and second secondary beams.

In another embodiment, a method of photoaltering a material is provided. The method includes phase shifting a pulsed laser beam to produce an input beam, holographically altering the input beam to produce a plurality of transmission beams, and scanning a portion of the material with the plurality of transmission beams.

BRIEF DESCRIPTION OF THE DRAWINGS

In the drawings, wherein like reference numerals refer to similar components:

FIG. 6 is a block diagram of an optical subsystem in accordance with one embodiment;

FIG. 7 is a block diagram of an optical subsystem in accordance with another embodiment;

DETAILED DESCRIPTION

The present invention provides systems and methods for photoaltering a material with multiple beam scanning. Photoalteration of a material may be accomplished using a pulsed laser beam that is directed (e.g., via a scanner) at a desired region of the material. For example, a pulsed laser beam may be controlled to scan the desired region and to create a separation of the material (e.g., which may be used to produce a flap of the material, to separate a portion of the material for transplants, or for a variety of other uses). With the systems and methods of the present invention, multiple output laser beams are optically derived from a single input laser beam, and these output laser beams are simultaneously scanned in the desired region. In one embodiment, the input laser beam is converted to multiple laser beams using a holographic optical element, and the multiple beams are then scanned in the desired region of the material. The term "holographic optical element" (HOE) is defined herein to be an optical element that controls the production of a plurality of beams from a source beam via diffraction. In another embodiment, the multiple beams are produced from the single input laser beam using phase-based optical subsystems.

Figure 1:
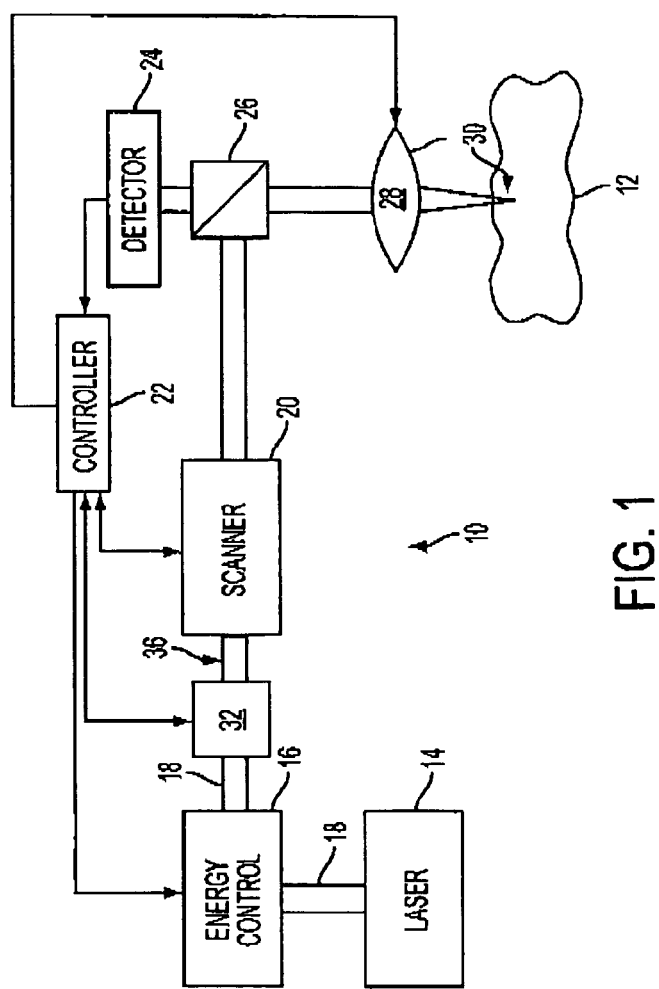
FIG. 1 is a block diagram of a laser scanner system in accordance with one embodiment of the present invention.

Referring to the drawings, a system 10 for photoaltering a material 12 is shown in FIG. 1. The system 10 includes, but is not necessarily limited to, a laser source 14 capable of generating a pulsed laser beam 18, an energy control module 16 for varying the pulse energy of the pulsed laser beam 18, an optical subsystem 32 for selectively converting the pulsed laser beam 18 to a plurality of beams 36 (e.g., multiple pulsed laser beams), a scanner 20, a controller 22, and focusing optics 28 that direct one or more focal points 30 of the pulsed laser beam 18 or the beams 36 onto the surface of or within the material 12 (e.g., sub-surface). The controller 22 (e.g., a processor operating suitable control software) communicates with one or more of the scanner 20, optical subsystem 32, and focusing optics 28 to control the direction of the focal point 30 as it is scanned along the material. In one scanning configuration, the optical subsystem 32 converts the pulsed laser beam 18 to the plurality of beams 36 which is then provided to the scanner 20. In another scanning configuration, the pulsed laser beam 18 passes through the optical subsystem 32 to the scanner 20. The system 10 may switch between these scanning configurations (e.g., by manual selection, automatic selection in response to a programmed scanning procedure, any combination of manual and automatic selection, or other selection).

In one embodiment, the optical subsystem 32 is manually inserted into or removed from the propagation path of the pulsed laser beam 18 to the scanner 20 to receive the pulsed laser beam 18. In another embodiment, the optical subsystem 32 is mechanically guided into the propagation path to capture the pulsed laser beam 18. Control signals may be automatically transmitted to the controller 22 (e.g., during execution of one or more programmed scanning procedures) or user input provided to the controller 22, which then actuates a servo component (not shown) coupled to the optical subsystem 32. Various combinations of automated and manual control of the optical subsystem 32 or other mechanisms may also be used to selectively produce the beams 36 from the pulsed laser beam 18 via the optical subsystem 32. In operation, the system 10 may have multiple scanning modes with at least one of the scanning modes engaging the optical subsystem 32 to produce the beams 36 when selected. The selective conversion of the pulsed laser beam 18 to the beams 36 using the optical subsystem 32 may thus be implemented in a variety of embodiments.

To impart at least a portion of the system control, software, firmware, or the like, can be used to command the actions and placement of the scanner via a motion control system, such as a closed-loop proportional integral derivative (PID) control system. In this embodiment, the system 10 further includes a beam splitter 26 and a detector 24 coupled to the controller 22 to provide a feedback control mechanism for the pulsed laser beam 18 or the beams 36. The beam splitter 26 and detector 24 may also be omitted in other embodiments, for example, with different control mechanisms.

The controller 22 includes computer hardware and/or software, often including one or more programmable processor unit running machine readable program instructions or code for implementing some or all of one or more of the methods described herein. The code is often embodied in a tangible media such as a memory (optionally a read only memory, a random access memory, a non-volatile memory, or the like) and/or a recording media (such as a floppy disk, a hard drive, a CD, a DVD, a memory stick, or the like). The code and/or associated data and signals may also be transmitted to or from the processor via a network connection (such as a wireless network, an Ethernet, an internet, an intranet, or the like), and some or all of the code may also be transmitted between components of the system 10 and within the controller via one or more bus, and appropriate standard or proprietary communications cards, connectors, cables, and the like will often be included in the controller. The controller 22 is often configured to perform the calculations and signal transmission steps described herein at least in part by programming the controller with the software code, which may be written as a single program, a series of separate subroutines or related programs, or the like. The controller 22 may include standard or proprietary digital and/or analog signal processing hardware, software, and/or firmware, and will typically have sufficient processing power to perform the calculations described herein during treatment of the patient. The controller 22 optionally includes a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

Movement of the focal point(s) 30 of the pulsed laser beam 18 or beams 36 is accomplished via the scanner 20 in response to the controller 22. In one embodiment, the scanner 20 scans the pulsed laser beam 18 or the beams 36 to produce an incision in the material. For a pre-determined scan rate, scanning the beams 36 to produce an incision reduces the overall scan time in comparison with scanning the single pulsed laser beam 18 to produce a substantially similar incision. For example, for a pre-determined scan spot distribution (e.g., as a result of scanning the beam 18 in a pre-determined area), a similar scan spot distribution can be more rapidly produced by scanning the beams 36 in the same area. When the optical subsystem 32 outputs the beams 36, the beams 36 are simultaneously scanned to more rapidly produce a similar distribution of scan spots.

To provide the pulsed laser beam 18, a chirped pulse laser amplification system, such as described in U.S. Pat. No. RE 37,585, may be used for photoalteration. U.S. Pat. Publication No. 2004/0243111 also describes other methods of photoalteration. Other devices or systems may be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point. The pulsed laser beam 18 is preferably linearly polarized, but may be configured in a different polarization state (e.g., circularly polarized).

Although the system 10 may be used to photoalter a variety of materials (e.g., organic, inorganic, or a combination thereof), the system 10 is suitable for ophthalmic applications in one embodiment. In this case, the focusing optics 28 direct the pulsed laser beam 18 toward an eye (e.g., onto a cornea) for plasma mediated (e.g., non-UV) photoablation of superficial tissue, or into the stroma for intrastromal photodisruption of tissue. In this embodiment, the system 10 may also include an applanation lens (not shown) to flatten the cornea prior to scanning the pulsed laser beam 18 toward the eye. A curved, or non-planar, lens may be substituted for the applanation lens to contact the cornea in other embodiments.

The system 10 is capable of generating the pulsed laser beam 18 with physical characteristics similar to those of the laser beams generated by a laser system disclosed in U.S. Pat. Nos. 4,764,930, 5,993,438, or the like. For example, the system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 18 has a wavelength that permits the pulsed laser beam 18 to pass through the cornea without absorption by the corneal tissue. The wavelength of the pulsed laser beam 18 is generally in the range of about 3 μm to about 1.9 nm, and preferably between about 400 nm to about 3000 nm. For accomplishing photodisruption of stromal tissues at the focal point, the irradiance of the pulsed laser beam 18 is preferably greater than the threshold for optical breakdown of the tissue. Although a non-UV, ultrashort pulsed laser beam is described in this embodiment, the pulsed laser beam 18 may have other pulse durations and different wavelengths in other embodiments.

Scanning is accomplished with the scanner 20 via the controller 22 by selectively moving the focal point(s) 30 to produce a structured scan pattern (e.g., a raster pattern, a spiral pattern, or the like) of scan spots. Operating the scanner 20 to scan this structured pattern is particularly useful for controlling the spacing between scan spots of the pattern. The step rate at which the focal point 30 is moved is referred to herein as the scan rate. For example, the scanner 20 can operate at scan rates between about 10 kHz and about 400 kHz, or at any other desired scan rate. In one embodiment, the scanner 20 generally moves the focal point of the pulsed laser beam 18 through the desired scan pattern at a substantially constant scan rate while maintaining a substantially constant separation between adjacent focal points. Further details of laser scanners are known in the art, such as described, for example, in U.S. Pat. No. 5,549,632, the entire disclosure of which is incorporated herein by reference.

In one embodiment, the scanner 20 includes, but is not necessarily limited to, a pair of scanning mirrors or other optics (not shown) to angularly deflect and scan one or more input beams (e.g, the pulsed laser beam 18 or beams 36). For example, scanning mirrors driven by galvanometers may be employed where each of the mirrors scans along different orthogonal axes (e.g., an x-axis and a y-axis). A focusing objective (not shown), having one or more lenses, images the input beam onto a focal plane of the system 10. The focal point 30 may thus be scanned in two dimensions (e.g., along the x-axis and the y-axis) within the focal plane of the system 10. Scanning along the third dimension, i.e., moving the focal plane along an optical axis (e.g., a z-axis), may be achieved by moving the focusing objective, or one or more lenses within the focusing objective, along the optical axis.

For ophthalmic applications (e.g., preparing a cornea for flap separation, corneal transplant, or the like), an area (e.g., substantially circular, oval, or other shape) may be scanned with a scan pattern based on the movement of the scanning mirrors. As the focal point 30 is scanned along a corneal bed, the pulsed laser beam 18 or beams 36 photoalter the stromal tissue. Using structured patterns, the distribution of scan spots is generally determined by the pulse frequency, the scan rate, the amount of scan line separation, and the number of beams 18, 36 selected for scanning. Generally, higher scan rates, enable shorter procedure times by increasing the rate at which corneal tissue can be photoaltered. For example, the scan rates may be selected from a range between about 30 MHz and about 1 GHz with a pulse width in a range between about 300 picoseconds and about 10 femtoseconds, although other scan rates and pulse widths may be used.

The system 10 may additionally acquire detailed information about optical aberrations to be corrected, at least in part, using the system 10. Examples of such detailed information include, but are not necessarily limited to, the extent of the desired correction, and the location in the cornea of the eye associated with the correction (e.g., where the correction can be made most effectively). The refractive power of the cornea may be used to indicate corrections. Wavefront analysis techniques, made possible by devices such as a Hartmann-Shack type sensor (not shown), can be used to generate maps of corneal refractive power. Other wavefront analysis techniques and sensors may also be used. The maps of corneal refractive power, or similar refractive power information provided by other means, such as corneal topographs or the like, can then be used to identify and locate the optical aberrations of the cornea that require correction.

In general, when the laser source 14 is activated, the focal spot 30 is selectively directed (e.g., via the scanner 20) along a beam path to photoalter stromal tissue. For example, the focal spot 30 is moved along a predetermined length of the beam path in one reference area. The pulsed laser beam 18 or beams 36 are then redirected through another reference area, and the process of photoalteration is repeated. The sequence for directing the pulsed laser beam 18 or beams 36 through individually selected reference areas can be varied, and the extent of stromal tissue photoalteration while the incising laser beam is so directed, can be varied. Specifically, as indicated above, the amount of photoalteration can be based on the refractive power map. On the other hand, the sequence of reference areas that is followed during a customized procedure will depend on the particular objectives of the procedure.

The scanner 20 may also scan a predetermined pattern using one or more scan patterns to one or more combinations of these reference areas or scan a single line (e.g., to produce a sidecut). One example of an ophthalmic scanning application is a laser assisted in-situ keratomilieusis (LASIK) type procedure where a flap is cut from the cornea to establish extracorporeal access to the tissue that is to be photoaltered. The flap may be created using random scanning or one or more scan patterns of pulsed laser beams. To create the corneal flap, a sidecut is created around a desired perimeter of the flap such that the ends of the sidecut terminate, without intersection, to leave an uncut segment. This uncut segment serves as a hinge for the flap. The flap is separated from the underlying stromal tissue by scanning the laser focal point across a resection bed, the perimeter of which is approximately defined by and slightly greater than the sidecut. Once this access has been achieved, photoalteration is completed, and the residual fragments of the photoaltered tissue are removed from the cornea. In another embodiment, the sidecut may be created completely around a desired perimeter (e.g., with the ends terminating with one another) to separate a portion of corneal tissue (e.g., for corneal transplant or the like) from the cornea. In another embodiment, intrastromal tissue may be photoaltered by the system 10 so as to create an isolated lenticle of intrastromal tissue. The lenticle of tissue can then be removed from the cornea.

Figure 2:
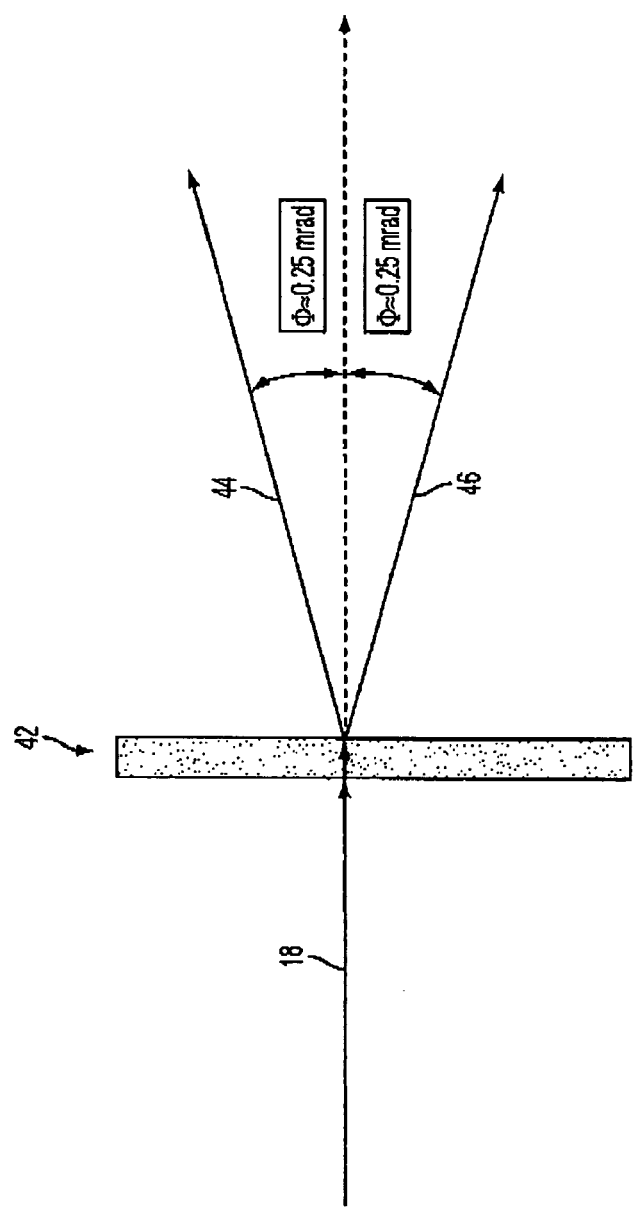
FIG. 2 is an elevational view of a holographic optical element in accordance with one embodiment.

FIG. 2 is an elevational view of a holographic optical element 42 in accordance with one embodiment. The holographic optical element 42 may be used as the optical subsystem 36, shown in FIG. 1. A first transmission beam 44 and a second transmission beam 46 are produced from an incident beam (i.e., the pulsed laser beam 18) on the holographic optical element 42. In this embodiment, the phase shift between grating lines of the holographic optical element 42 is about one-hundred and eighty degrees (180°) and results in secondary order diffracted beams from the incident beam while suppressing the zero order. The secondary order diffracted beams (e.g., the −1 and +1 order) have about eighty percent (80%) of the energy of the incident beam. Multi-level holographic optical elements can be produced which have lower losses (e.g., approaching about ninety-seven percent (97%) efficiency). The holographic optical element 42 may be constructed to vary the angle of departure (i.e., from the angle of the incident beam) of the transmission beams 44, 46 as well as the number of output beams.

For example, each of the transmission beams 44, 46 may have a departure angle of about 0.25 rad from the incidence angle. In this example, the intensity ($I_1$) associated with the first transmission beam 44 is substantially similar to the intensity ($I_2$) associated with the second transmission beam 46 (e.g., an average deviation from intensity symmetry of about 5%), and the average intensity associated with the transmission beams 44, 46 is greater than about 80% (e.g., $(I_1+I_2)/I_0$) where $I_0$ is the intensity associated with the pulsed laser beam 18). Total losses of the output beams 44, 46 in comparison with the pulsed laser beam 18 are less than about 200%. Thus, multiple beams are provided by the holographic optical element 42 from the pulsed laser beam 18, which may then be scanned to form an incision.

Figure 3:
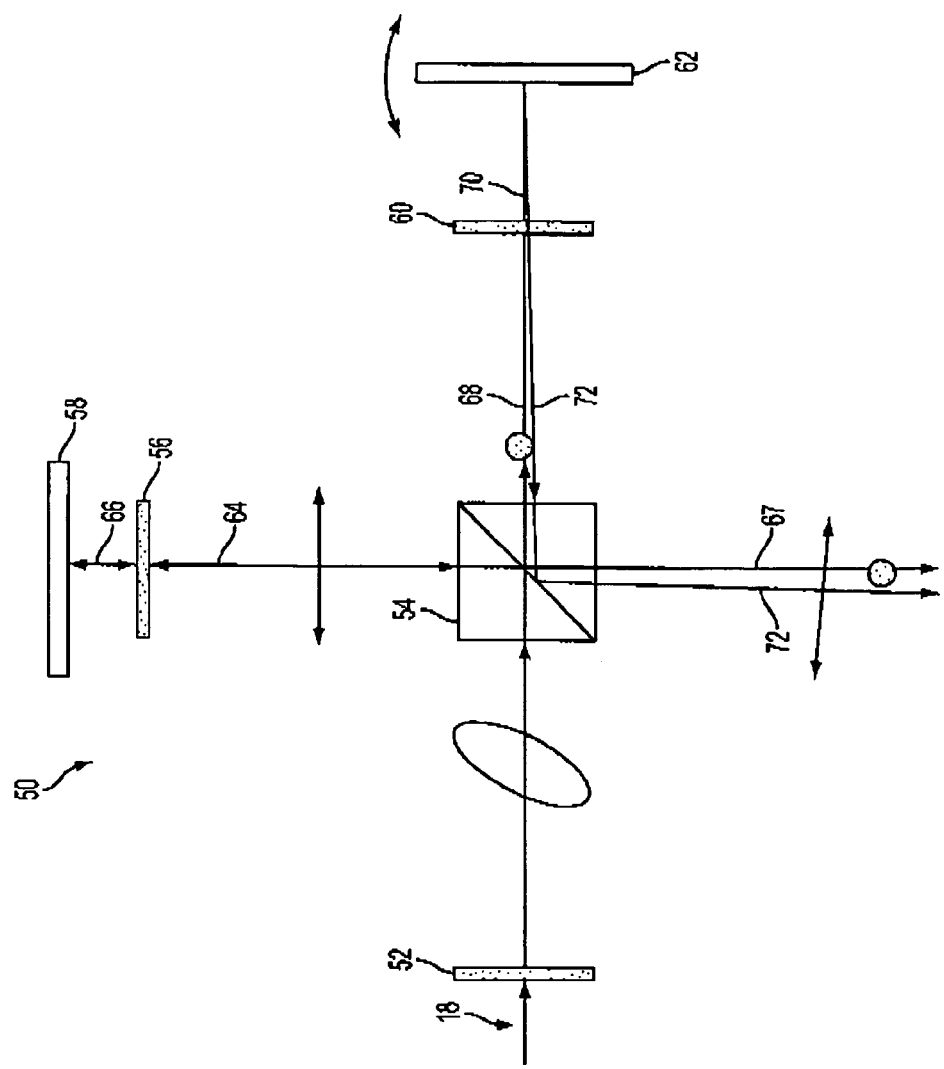
FIG. 3 is a block diagram of an optical subsystem in accordance with one embodiment.

FIG. 3 is a block diagram of an optical subsystem 50 in accordance with one embodiment. In this embodiment, the optical subsystem 50 includes, but is not necessarily limited to, a first quarter-wave plate 52, a first polarizing beam splitter 54, and an optics arrangement configured to produce a first transmission beam 67 and a second transmission beam 72 based on a beam incident on the quarter-wave plate 52, such as the pulsed laser beam 18. Thus, the optical subsystem 50 provides two beams (e.g., the transmission beams 67 and 72) from a single beam (e.g., the pulsed laser beam 18), which may then be scanned, such as using the scanner 20 shown in FIG. 1.

A wave plate or retarder is an optical device that alters the polarization state of an input light wave traveling therethrough. In one embodiment, the wave plate operates by shifting the phase of the input light wave between two perpendicular polarization components. One example of a wave plate is a birefringent crystal having a a pre-determined thickness. This crystal is typically cut such that the extraordinary axis (i.e., polarized parallel to the axis of anisotropy) is parallel to the surfaces of the wave plate. When the extraordinary index is less than the ordinary (i.e., polarized perpendicularly to the axis of anisotropy) index, such as in calcite, the extraordinary axis is referred to as the "first axis," and the ordinary axis is referred to as the "slow axis." In general, light polarized along the first axis propagates faster than light polarized along the slow axis. Depending on the thickness of the crystal, input light with polarization components along both axes emerge from the crystal in a different polarization state.

The wave plate is characterized by the amount of relative phase imparted on the two polarization components, which is related to the birefringence and the thickness of the crystal. For example, a quarter-wave plate creates a quarter wavelength phase shift and can change linearly polarized light to circular and vice versa (e.g., by adjusting the plane of the incident light to about a 45° angle with the fast axis). The resulting light has equal amplitude ordinary and extraordinary waves. A half-wave plate retards one polarization component by a half wavelength, or 180°, and thus rotates the polarization direction of linear polarized light.

In operation, the quarter-wave plate 52 converts the pulsed laser beam 18 from linear polarization to circular polarization, or more particularly, a circularly polarized pulsed laser beam. The polarizing beam splitter 54 receives the circularly polarized light and reflects light having one polarization (e.g., a first polarized beam 64) while transmitting light having a different polarization (e.g., a second polarized beam 68) than the reflected light. The first polarized beam 64 (e.g., linearly polarized along the plane of FIG. 3) is reflected to a first optics group of the optics assembly, and the second polarized beam 68 (e.g., linearly polarized in/out of the plane of FIG. 3) is transmitted to a second optics group of the optics assembly.

The first optics group includes a second quarter-wave plate 56 and a first mirror reflector 58. The first polarized beam 64 is incident on the quarter-wave plate 56, which converts the first polarized beam 64 to a circularly polarized beam 66, and the mirror reflector 58 reflects the circularly polarized beam 66 back to the quarter-wave plate 56, which converts the circularly polarized beam 66 to the first transmission beam 67. The first transmission beam 67 is linearly polarized orthogonal to the first polarized beam 64 (e.g., linearly polarized in/out of the plane of FIG. 3) and is transmitted through the polarizing beam splitter 54 to the scanner 20.

The second optics group includes a third quarter-wave plate 60 and a second mirror reflector 62 that is tiltable or may be pivoted. The second polarized beam 68 is incident on the quarter-wave plate 60, which converts the second polarized beam 68 to a circularly polarized beam 70, and the mirror reflector 62 reflects the circularly polarized beam 70 back to the quarter-wave plate 60, which converts the circularly polarized beam 70 to the second transmission beam 72. The second transmission beam 72 is linearly polarized orthogonal to the second polarized beam 68 (e.g., linearly polarized along the plane of FIG. 3) and is reflected by the polarizing beam splitter 54 to the scanner 20. The first transmission beam 67 is angularly separated, and preferably divergent, from the second transmission beam 72 by the degree of tilt or pivot of the second mirror reflector 62, thereby controlling the separation between the focal points of the transmission beams 67, 72.

Figure 4:
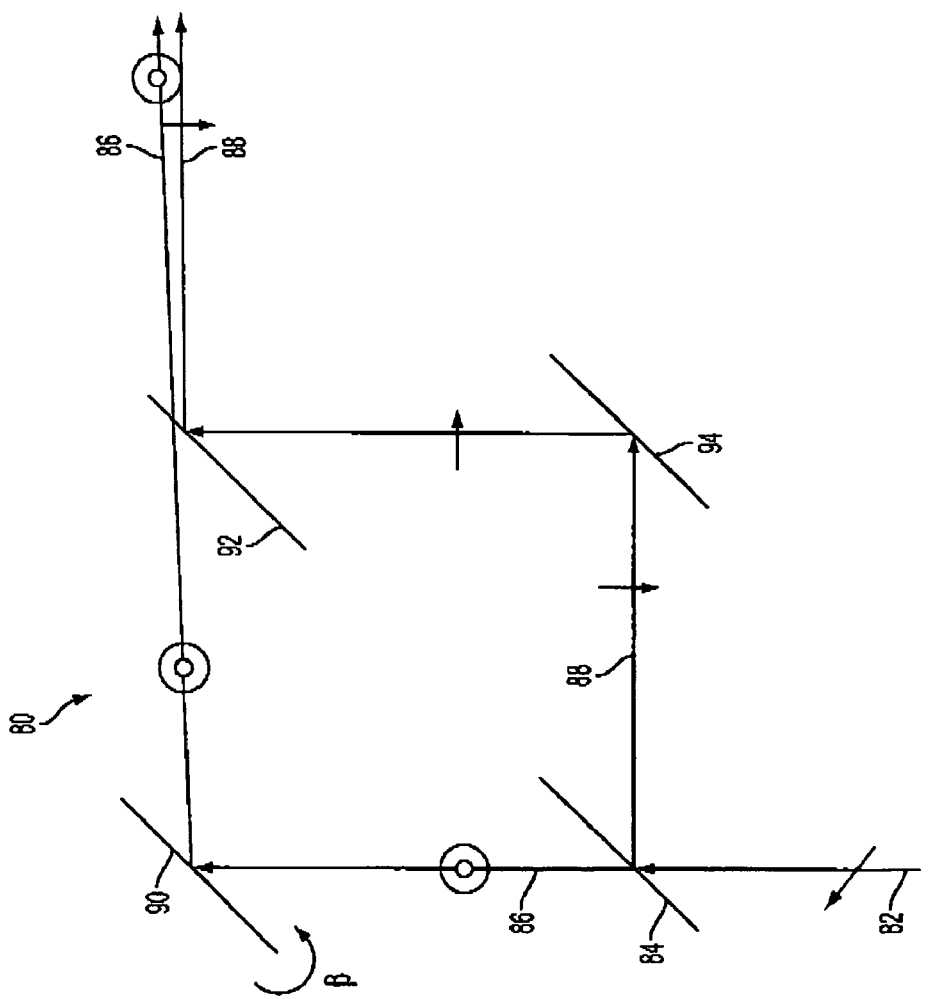
FIG. 4 is a block diagram of an optical subsystem in accordance with another embodiment.

FIG. 4 is a block diagram of an optical subsystem 80 in accordance with another embodiment. In this embodiment, the optical subsystem 80 includes, but is not necessarily limited to, a first polarizing beam splitter 84, a first mirror reflector 90 that is tiltable or may be pivoted, a second mirror reflector 94, and a second polarizing beam splitter 92. In one embodiment, a beam 82 incident on the polarizing beam splitter 84, such as the pulsed laser beam 18, may have a polarization of about 45°±θ where θ is selected for intensity ratio control. The polarizing beam splitters 84 and 94 are configured to reflect light having one polarization while transmitting light having a different polarization than the reflected light. For example, the polarizing beam splitter 84 transmits a first polarized beam 86 (e.g., linearly polarized in/out of the plane of FIG. 4) to the mirror reflector 90 and reflects a second polarized beam 88 (e.g., linearly polarized along the plane of FIG. 4) to the mirror reflector 92. Both of the polarized beams 86 and 88 are based on the incident beam 82. The mirror reflector 90 reflects the first polarized beam 86 to the polarizing beam splitter 94, and the mirror reflector 92 reflects the second polarized beam 88 to the polarizing beam splitter 94. The polarizing beam splitter 94 transmits the first polarized beam 86 and reflects the second polarized beam 88. Thus, the optical subsystem 80 provides two beams (e.g., the polarized beams 86 and 88) from a single beam (e.g., the pulsed laser beam 18), which may be provided to the scanner 20 shown in FIG. 1.

Figure 5:
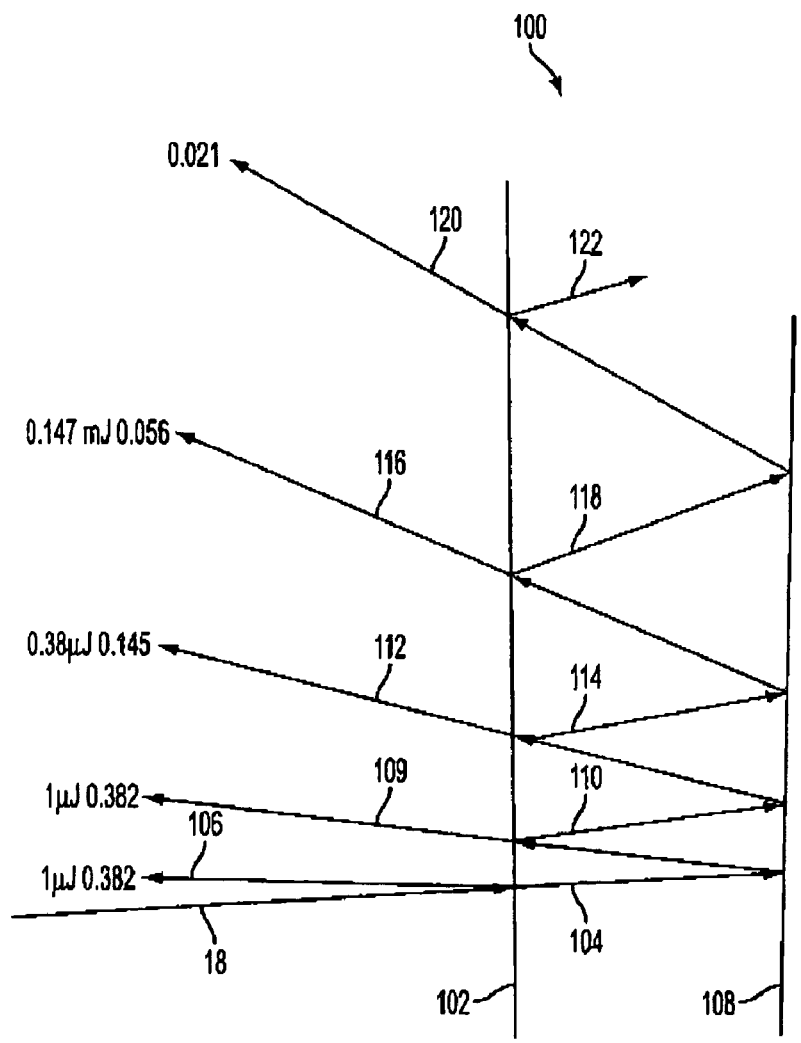
FIG. 5 is a block diagram of an optical subsystem in accordance with another embodiment.

The first polarized beam 86 is angularly separated, and preferably divergent, from the second polarized beam 88 by the degree of tilt or pivot of the mirror reflector 90, thereby controlling the separation between the focal points of the polarized beams 86, 88. Although this embodiment of the optical subsystem 80 generates two focal points (or two beams from a single beam), a different numbers of focal points (or multiple beams from a single beam) can be generated in other embodiments. For example, a tandem embodiment based on the optical subsystem 80 (e.g., series or parallel combinations of two of the optical subsystem 80) can be used to generate 4 focal points FIG. 5 is a block diagram of an optical subsystem 100 in accordance with another embodiment. The optical subsystem 100 is based on a Fizeau wedge to produce two transmission beams from a single incident beam. A Fizeau wedge is generally formed by two optical elements at an angle to one another. Typically, an incident beam impinges on the front surface of the Fizeau wedge at an angle with the normal to the front surface. As this beam passes into the wedge, a portion of the incident beam is refracted as a second beam through the thickness of the wedge. The other portion of the incident beam not entering the wedge is reflected from the front surface. The second beam impinges on the internal side of the rear surface of the wedge and is reflected off the internal side of the rear surface towards the internal side of the front surface. Part of the reflected second beam exits the front surface of the wedge as a third beam. The other part of the reflected second beam is reflected back off the internal side of the front surface to the rear surface of the wedge as a fourth beam.

In this embodiment, the optical subsystem 100 includes, but is not necessarily limited to, an optical element 102 and a mirror reflector 108 oriented at a predetermined angle with respect to the optical element 102. This angle may be adjusted depending on a desired focal point separation between at least two transmission beams. The optical element 102 has a predetermined reflectivity (R) that allows a majority of the incident light to pass through the optical element 102. In one embodiment, the reflectivity is about $0.382 [R=(3/2^2)/2=0.382?]$, although the optical element 102 may be configured with other values of reflectivity.

Based on this reflectivity, the optical element 102 reflects a portion of a beam incident on the optical element 102 (e.g., the pulsed laser beam 18) and transmits another portion of the beam 18. For example, the optical element 102 reflects a first beam 106 while reflecting a second beam 104, where both the first and second beams 106 and 104 are based on the beam 18. The mirror reflector 108 reflects the second beam 104 back to the optical element 102, and the optical element 102 transmits a portion of the second beam 104 while reflecting another portion of the second beam 104 based on the reflectivity, R. For example, the optical element 102 transmits a third beam 109 while reflecting a fourth beam 110, where both of the beams 109 and 110 are based on the second beam 104. This reflection by mirror reflector 108 and partial transmission and reflection by optical element 102 can continue indefinitely. For example, the mirror reflector 108 reflects the fourth beam 110 back to the optical element 102. Based on the reflectivity, R, and the fourth beam 110, the optical element 102 transmits a fifth beam 112 while reflecting a sixth beam 114. The mirror reflector 108 reflects the sixth beam 114 back to the optical element 102. Based on the reflectivity, R, and the sixth beam 114, the optical element 102 transmits a seventh beam 116 while reflecting an eighth beam 118. The mirror reflector 108 reflects the eighth beam 118 back to the optical element 102. Based on the reflectivity, R, and the eighth beam 118, the optical element 102 transmits a ninth beam 120 while reflecting a tenth beam 122.

In this embodiment, the first and third beams 106 and 109 have substantially similar intensities, and the spacing between the focal points of the beams 106 and 109 may be controlled by the angle between the optical element 102 and the mirror reflector 108. The beams other than the first and third beams 106 and 109 (e.g., the beams 112, 116, 120) produced by the optical subsystem 100 have intensities (e.g., per pulse) that are substantially diminished from the intensities associated with each of the first and third beams 106 and 109. For example, when the first and third beams 106 and 109 each have an intensity of about 1 µJ, the intensity of the fifth beam 112 may be represented by about 0.38 µJ, and the intensity of the seventh beam may be represented by about 0.147 µJ. The total percentage energy loss associated with the beams 112, 116, 120 can be represented by $(0.145+0.056+0.021+ \ldots)*100=23.6\%$. In a non-overlapping scanning procedure (e.g., non-overlapping focal points of adjacent scan spots), the beams other than the first and third beams 106 and 109 (e.g., the beams 112, 116, 120) are preferably not used for scanning. Thus, multiple beams 106, 109 are produced from the single pulsed laser beam 18 and can be directed to the scanner 20, shown in FIG. 1.

FIG. 6 is a block diagram of an optical subsystem 130 in accordance with one embodiment. In this embodiment, the optical subsystem 130 includes, but is not necessarily limited to, a half-wave plate 132 and a Wollaston prism 136 configured to produce a first transmission beam 140 and a second transmission beam 142 based on a beam incident on the half-wave plate 132, such as the pulsed laser beam 18. Thus, the optical subsystem 130 provides two beams (e.g., the transmission beams 140 and 142) from a single beam (e.g., the pulsed laser beam 18), which may then be scanned, such as using the scanner 20 shown in FIG. 1.

In general, a Wollaston prism manipulates polarized light by separating randomly polarized or unpolarized light into two orthogonal, linearly polarized outgoing beams. In one configuration, the Wollaston prism includes two calcite prisms that are coupled together to form two right trianglular prisms with orthogonal optical axes. Outgoing light beams diverge from the Wollaston prism resulting in the two differently polarized beams, with the angle of divergence determined by the prisms' wedge angle and the wavelength of the light. For example, light striking the surface of incidence at right angles is refracted in a first prism (e.g., the first of the two coupled prisms encountered along the propagation direction) into an ordinary beam (O) and an extraordinary beam (A). However, these two beams continue to propagate in the same direction. With the optical axis of the second prism being perpendicular to the optical axis of the first prism, the ordinary beam (O) becomes an extraordinary beam at the boundary surface (e.g., between the two prisms). The opposite applies to the original extraordinary beam (A), which becomes an ordinary beam.

In this embodiment, the half-wave plate 132 changes the polarization direction of light incident on the half-wave plate 132 (e.g., the pulsed laser beam 18). By retarding one polarization component of the pulsed laser beam 18 by a half wavelength, the linear polarized light is rotated to produce a first beam 134. At a boundary interface 138 of the Wollaston prism 136, the first transmission beam 140 (e.g., linearly polarized along the plane of FIG. 6) and the second transmission beam 142 (e.g., linearly polarized in/out of the plane of FIG. 6) are produced from the first beam 134 and angularly separated by $\phi$. In one embodiment, the Wollaston prism 136 is constructed to produce an angle of separation $\phi=6$, although the angle of separation may vary in other embodiments. Each of the transmission beams 140 and 142 has an intensity associated therewith, $I_1$ and $I_2$, respectively, and the intensity ratio of $I_1/I_2$ can be continuously adjusted by the half-wave plate 132 (e.g., to provide a substantially unity ratio).

FIG. 7 is a block diagram of an optical subsystem 150 in accordance with another embodiment. The optical subsystem 150 includes tandem Wollaston prisms 152 and 154 to provide four beams (e.g., a first transmission beam 160, a second transmission beam 162, a third transmission beam 164, and a fourth transmission beam 166) from a single beam (e.g., the pulsed laser beam 18), which may then be scanned, such as using the scanner 20 shown in FIG. 1. In this embodiment, a first Wollaston prism 152 has orthogonal optical axes, and a second Wollaston prism 154 has optical axes that are orthogonal to one another and together rotated about 45° from the optical axes of the first Wollaston prism 152. In operation, the first Wollaston prism 152 receives the pulsed laser beam 18 and produces a first intermediate beam 154 having a first polarization and a second intermediate beam 156 having a second polarization orthogonal to the first polarization. The second Wollaston prism 158 produces the first and second transmission beam 160 and 162, respectively, from the first intermediate beam 154 and the third and fourth transmission beam 164 and 166, respectively, from the second intermediate beam 156. The first and second transmission beams 160 and 162 have orthogonal polarizations, and the third and forth transmission beams 164 and 166 have orthogonal polarizations.

Figure 8:
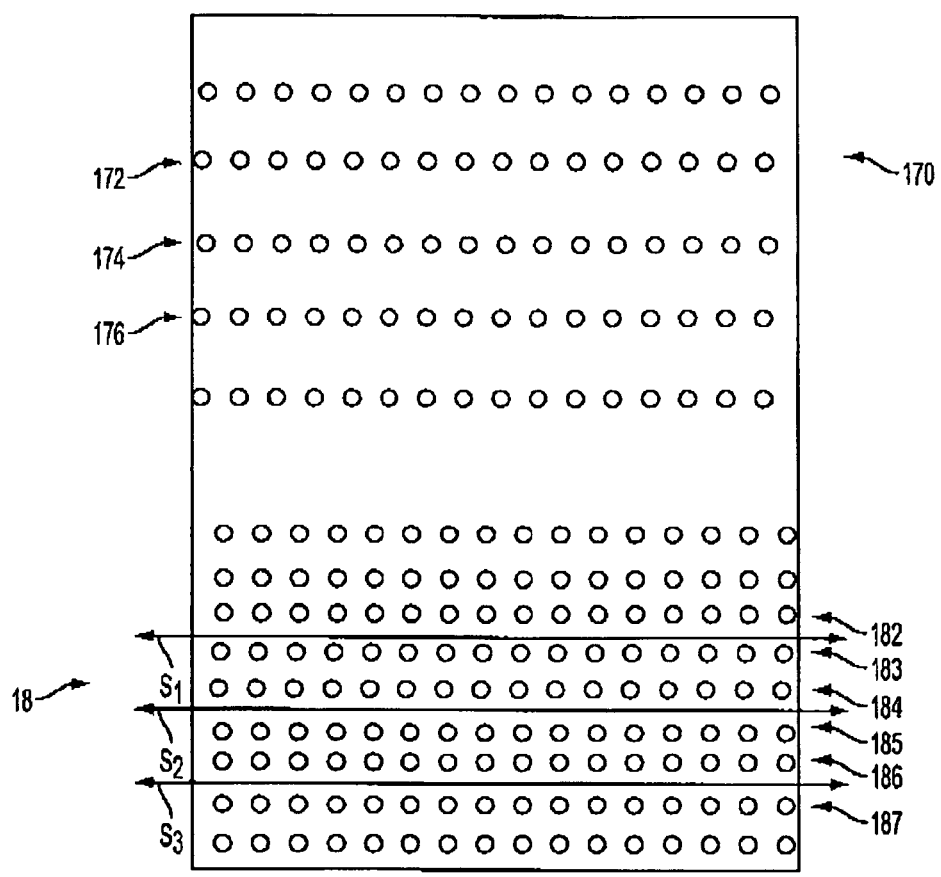
FIG. 8 is a top view of raster patterns formed in a material in accordance with one embodiment.

FIG. 8 is a top view of raster scan patterns 170, 180 formed on a material (e.g., glass) in accordance with one embodiment. Referring to FIGS. 1 and 8, the pulsed laser beam 18 may be directed (e.g., without producing multiple beams by the optical subsystem 32) to the scanner 20 to produce the raster scan pattern 170. The raster scan pattern 170 has multiple raster lines 172, 174, 176, each corresponding to a different scan line, and each raster line 172, 174, 176 is formed from multiple spots. The raster scan pattern 170 was formed in glass with a 60 kHz laser and has a spot separation of about 7 μm (i.e., between adjacent spots along a raster line) and a scan line separation of about 14 μm (i.e., between adjacent raster lines).

When the optical subsystem 32 produces the multiple beams 36 from the pulsed laser beam 18, the beams 36 are directed to the scanner 20 to produce the raster scan pattern 180. The raster scan pattern 180 has multiple pairs of raster lines, such as a first pair of raster lines 182 and 183, a second pair of raster lines 184 and 185, and a third pair of raster lines 186 and 187, and each raster line 132, 183, 184, 185, 186, and 187 is formed from multiple spots. Each of the pairs of raster lines 182 and 183, 184 and 185, 186 and 187 corresponds to a different scan line. For example, the scanner 20 scans along a first scan line ($S_1$) to produce the first pair of raster lines 182 and 183, along a second scan line ($S_2$) to produce the second pair of raster lines 184 and 185, and along a third scan line ($S_3$) to produce the third pair of raster lines 186 and 187. The raster scan pattern 180 was also formed in glass with the 60 kHz laser and has a spot separation of about 7 μm (i.e., between adjacent spots along a raster line) and a scan line separation of about 14 μm (i.e., between the adjacent scan lines). Using the optical subsystem 32 to produce the multiple beams 36 effectively doubles the scan spots and/or the raster lines while scanning at the same rate in comparison to scanning with the pulsed laser beam 18 to produce the raster scan pattern 170. Thus, for a pre-determined scan rate, the scan spots within a desired scan region can be increased without incurring additional scan time using the optical subsystem 32. Additionally, for a pre-determined scan rate and scan spot distribution, the total scan time can be decreased using the optical subsystem 32.

Figure 9:
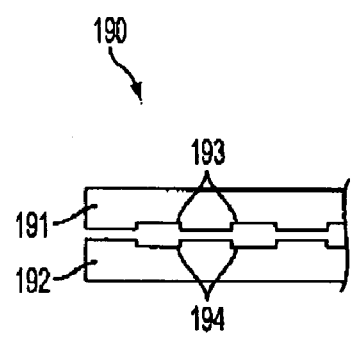
FIG. 9 is a side view of an optical subsystem in accordance with one embodiment illustrating an "ON" configuration.
Figure 10:
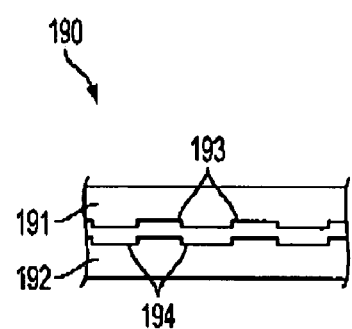
FIG. 10 is a side view of the optical subsystem shown in FIG. 9 illustrating an "OFF" configuration.

The optical subsystem 32 may also be configured to dynamically modify the pulsed laser beam 18 to produce the multiple beams 36. FIG. 9 is a side view of an optical subsystem 190 in accordance with one embodiment illustrating an "ON" configuration. FIG. 10 is a side view of the optical subsystem 190 shown in FIG. 9 illustrating an "OFF" configuration. Referring to FIGS. 1, 9, and 10, the optical subsystem 190 may be implemented with the system 10 (e.g., substituted for the optical subsystem 32) and includes a first phase grating 191 substantially adjacent to a second phase grating 192. Each of the phase gratings 191, 192 has grooves 193 and 194, respectively, with a periodicity based on the wavelength of the pulsed laser beam 18. The grooves 193 of the first phase grating 191 face the grooves 194 of the second phase grating 192. In the ON configuration shown in FIG. 9, the grooves 193 are aligned with the grooves 194 to phase shift the pulsed laser beam 18 and thereby produce multiple beams, such as the beams 44 and 46 shown in FIG. 2. In the OFF configuration, the grooves 193 are staggered with respect to the grooves 194 to shift light associated with each of the grooves 193, 194 by about a half period and thereby prevent the production of multiple beams. Thus, the phase gratings 191 and 192 may be positioned with respect to one another to produce multiple beams from the pulsed laser beam 18 (e.g., using the ON configuration) or to pass the pulsed laser beam 18 (e.g., using the OFF configuration). The phase gratings 191 and 192 may also be positioned between the ON and OFF configurations to create a compound phase pattern.

Thus, systems and methods of photoaltering a material with multiple pulsed laser beams originating from a single input pulsed laser beam are disclosed. The systems and methods are suited to remove material, photoalter corneal tissue, micromachine materials, surface profile various biological tissues, or the like. Examples of some refractive eye surgery applications for the system 10 include, but are not necessarily limited to, photorefractive keratectomy (PRK), LASIK, laser assisted sub-epithelium keratomileusis (LASEK), or the like. The optical subsystem 32 is simple to implement and integrate within the system 10 and improves the effective repetition rate of the pulsed laser beam by at least a factor of 2, 3, or greater. When the optical subsystem 32 is used in the system 10, at least one of the following advantages may result: the overall procedure time associated with scanning is decreased, the energy associated with each scan spot is decreased, the relative smoothness of the scan bed is improved, and the scanning speed of the galvo is reduced.

While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A system for photoaltering corneal stromal tissue to separate of the stromal tissue, the system comprising:
    a laser source operable to produce a primary pulsed beam having an irradiance greater than a threshold for optical breakdown of the stromal tissue;
    a first optical element configured to receive the primary pulsed beam and transmit a first secondary beam, the first secondary beam based on the primary pulsed beam and phase shifted from the primary pulsed beam by about a first quarter wavelength;
    a first polarizing beam splitter configured to reflect a first polarized beam and transmit a second polarized beam, the first and second polarized beams together based on the first secondary beam;
    a subsystem configured to produce a first transmission beam and a second transmission beam based on the first and second polarized beams, the first transmission beam angularly separated from the second transmission beam, the subsystem comprising:
        a second optical element configured to receive the first polarized beam and transmit a second secondary beam, the second secondary beam based on the first polarized beam and phase shifted from the first polarized beam by about a second quarter wavelength;
        a first mirror configured to reflect the second secondary beam to a second wave plate, the second wave plate further configured to transmit the first transmission beam;
        a third optical element configured to receive the second polarized beam and transmit a third secondary beam, the third secondary beam based on the second polarized beam and phase shifted from the second polarized beam by about a third quarter wavelength; and
        a second mirror configured to reflect the third secondary beam to a third wave plate, the third wave plate further configured to transmit the second transmission beam;
    a scanner operable to direct the first and second transmission beams to the material for plasma mediated photoablation of the stromal tissue; and
    a controller communicating with the scanner to control the direction of the transmission beams to create a separation of the stromal tissue based on a structured pattern of scan spots associated with the transmission beams.

2. The system of claim 1, wherein each of the first, second, and third optical elements comprises a quarter wave plate.

3. The system of claim 1, wherein the second mirror is further configured to pivot to angularly separate the first transmission beam from the second transmission beam.

4. The system of claim 1, wherein the first polarizing beam splitter is further configured to transmit the first transmission beam from the second wave plate and reflect the second transmission beam from the third wave plate.

5. A system for photoaltering corneal stromal tissue to separate a portion of the tissue, the system comprising:
    a laser source operable to produce a primary pulsed beam having an irradiance greater than a threshold for optical breakdown of the stromal tissue;
    a first optical element configured to receive the primary pulsed beam and transmit a first secondary beam, the first secondary beam based on the primary pulsed beam and phase shifted from the primary pulsed beam by about a first quarter wavelength;
    a first polarizing beam splitter configured to reflect a first polarized beam and transmit a second polarized beam, the first and second polarized beams together based on the first secondary beam;
    a subsystem configured to produce a first transmission beam and a second transmission beam based on the first and second polarized beams, the first transmission beam angularly separated from the second transmission beam, the subsystem comprising:
        a first mirror configured to reflect the first polarized beam;
        a second mirror configured to reflect the second polarized beam; and
    a second polarizing beam splitter configured to:
        receive the first polarized beam from the first mirror and the second polarized beam from the second mirror;
        transmit the first polarized beam to the scanner, the first polarized beam being the first transmission beam; and
        reflect the second polarized beam to the scanner, the second polarized beam being the second transmission beam;
    a scanner operable to direct the first and second transmission beams to the material for plasma mediated photoablation of the stromal tissue; and
    a controller communicating with the scanner to control the direction of the transmission beams to create a separation of the stromal tissue based on a structured pattern of scan spots associated with the transmission beams.

6. The system of claim 5, wherein the first mirror is further configured to pivot to angularly separate the first transmission beam from the second transmission beam.

* * * * *